US011707046B2

(12) United States Patent
Capo

(10) Patent No.: US 11,707,046 B2
(45) Date of Patent: Jul. 25, 2023

(54) *PETUNIA* VARIETY 'KLEPH20580'

(71) Applicant: Klemm+Sohn GmbH & Co. KG, Stuttgart (DE)

(72) Inventor: Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/538,605

(22) Filed: Nov. 30, 2021

(65) Prior Publication Data

US 2022/0192139 A1 Jun. 23, 2022

Related U.S. Application Data

(60) Provisional application No. 63/129,276, filed on Dec. 22, 2020.

(51) Int. Cl.
*A01H 6/82* (2018.01)
*A01H 5/02* (2018.01)
*A01H 5/10* (2018.01)

(52) U.S. Cl.
CPC .............. *A01H 6/824* (2018.05); *A01H 5/02* (2013.01); *A01H 5/10* (2013.01)

(58) Field of Classification Search
USPC ......................................... Plt./356.1, 356.13
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A *Petunia* plant designated KLEPH20580 is disclosed. Embodiments include seeds of *Petunia* KLEPH20580, plants of *Petunia* KLEPH20580, to plant parts of *Petunia* KLEPH20580, and methods for producing a plant by crossing *Petunia* KLEPH20580 with itself or with another variety. Embodiments also relate to *Petunia* varieties, breeding varieties, plant parts, and cells derived from *Petunia* KLEPH20580, methods for producing other *Petunia* lines or plant parts derived from *Petunia* KLEPH20580, and the *Petunia* plants, varieties, and their parts derived from use of those methods. Embodiments further include hybrid *Petunia* seeds, plants, and plant parts produced by crossing *Petunia* KLEPH20580 with another *Petunia* variety or another plant type.

27 Claims, 1 Drawing Sheet
(1 of 1 Drawing Sheet(s) Filed in Color)

PETUNIA VARIETY 'KLEPH20580'

CROSS-REFERENCE TO RELATED APPLICATIONS

This application claims priority to and the benefit of U.S. Provisional Application No. 63/129,276, filed on Dec. 22, 2020, the entire contents of which are incorporated herein by reference for all purposes.

BACKGROUND

All publications cited in this application are herein incorporated by reference. *Petunia* is a species of flowering plants in the family Solanaceae.

*Petunia* can be propagated from seed, cuttings, and tissue culture. Seed, cuttings and tissue culture germination protocols for *Petunia* are well-known in the art.

*Petunia* is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior *Petunia* varieties.

The foregoing examples of the related art and limitations related therewith are intended to be illustrative and not exclusive. Other limitations of the related art will become apparent to those of skill in the art upon a reading of the specification.

BRIEF DESCRIPTION OF THE FIGURE

The patent or application file contains one or more drawings executed in color and/or one or more photographs. Copies of this patent or patent application publication with color drawing(s) and/or photograph(s) will be provided by the Patent Office upon request and payment of the necessary fee.

The accompanying FIGURE, which is herein incorporated and form a part of the specification, illustrate some, but not the only or exclusive example embodiments and/or features. It is intended that the embodiments and FIGURE disclosed herein are intended to be illustrative rather than limiting.

The photo shows the overall plant habit of the plant grown in a pot, including the flowers, buds, and foliage.

SUMMARY

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to one embodiment, there is provided a *Petunia* plant which is valued as breeding line enabling the development of superior ornamental *Petunia* plants.

Another embodiment discloses a *Petunia* plant, wherein a sample of representative sample of plant tissue of said *Petunia* is deposited with a Budapest depository.

Another embodiment relates to tissue culture produced from protoplasts or cells from the *Petunia* plants disclosed in the subject application, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, and stems.

Another embodiment relates to a plant, or a part thereof, produced by *Petunia* KLEPH20580, wherein the plant part comprises at least one cell of *Petunia* KLEPH20580.

Another embodiment relates to a tissue or cell culture of regenerable cells produced from the plant of KLEPH20580 and a *Petunia* plant regenerated from the tissue or cell culture of KLEPH20580.

Another embodiment relates to a method of vegetatively propagating the plant of KLEPH20580, comprising the steps of: collecting tissue or cells capable of being propagated from a plant of KLEPH20580; cultivating said tissue or cells of the prior step to obtain proliferated shoots or plantlets; and rooting said proliferated shoots or plantlets to obtain rooted shoots or rooted plantlets.

A further embodiment relates to a method for producing an embryo or seed, wherein the method comprises crossing a KLEPH20580 plant with another plant and harvesting the resultant embryo or seed. For example, the other plant could either be a *Petunia* plant or a *Calibrachoa* plant.

A further embodiment relates to a method for developing a *Petunia* plant in a *Petunia* plant breeding program, comprising applying plant breeding techniques comprising crossing, recurrent selection, mutation breeding, wherein said mutation breeding selects for a mutation that is spontaneous or artificially induced, mass selection, hybridization, open-pollination breeding, backcrossing, pedigree breeding, or genetic marker enhanced selection to the *Petunia* plant of KLEPH20580, or its parts, wherein application of said techniques results in development of a *Petunia* plant.

A further embodiment relates to a method of introducing a mutation into the genome of *Petunia* plant KLEPH20580, said method comprising mutagenesis of the plant, or plant part thereof, of KLEPH20580, wherein said mutagenesis is selected from the group consisting of temperature, long-term seed storage, tissue culture conditions (i.e., somaclonal variation), radiation, mutagens, and targeting induced local lesions in genomes, and wherein the resulting plant comprises at least one genome mutation and producing plants therefrom.

A further embodiment relates to a method of editing the genome *Petunia* plant KLEPH20580, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

A further embodiment relates to a *Petunia* seed produced by growing KLEPH20580.

A further embodiment relates to a method of producing a *Petunia* plant, or part thereof, by growing a seed produced on KLEPH20580.

In addition to the exemplary aspects and embodiments described above, further aspects and embodiments will become apparent by study of the following descriptions.

DETAILED DESCRIPTION

Origin of KLEPH20580

KLEPH20580 originated from a cross-pollination conducted in April 2018 in Latina, Italy between the commercial *Petunia* variety 'Wespebimost', also known commercially as CRAZYTUNIA 'Moonstruck' (U.S. Plant Patent pending) and the proprietary male *Petunia* variety 'PH-2017-2906' (unpatented).

The seeds from the cross were sown and plants were grown in a greenhouse for evaluation, where an individual plant designated KLEPH20580 was selected from the group of plants. In May 2018, KLEPH20580 was first vegetatively propagated by terminal tip cuttings and tissue culture in Latina, Italy. KLEPH20580 was found to reproduce true to type in successive generations of asexual propagation via tissue culture and terminal tip cuttings (vegetative cuttings) with careful attention to uniformity of plant type and has been increased with continued observation for uniformity. Additionally, *Petunia* variety KLEPH20580 produces viable pollen and is capable of being used as a parental line in breeding programs. KLEPH20580 exhibits a unique spotted flower color pattern of white dots with magenta-colored flowers, a white center, and a slight petal margin.

The data which define these characteristics were collected from asexual reproductions carried out in Latina, Italy. Data was collected on plants grown 13-weeks from cultivation from potting in a plastic greenhouse. Color references are to The R.H.S. Colour Chart of The Royal Horticultural Society of London (R.H.S.), 5$^{th}$ edition (2007).

TABLE 1

VARIETY DESCRIPTION INFORMATION

Classification:

Family: Solanaceae
Botanical: *Petunia hybrida*
Common: Petunia
Designation: 'KLEPH20580'
Parentage:

Female parent: The *Petunia* variety 'Wespebimost', also known commercially as CRAZYTUNIA 'Moonstruck' (U.S. Plant Patent pending)
Male parent: The proprietary male *Petunia* variety 'PH-2017-2906' (unpatented)
Plant:

Vigor: Medium vigor
Habit: Semi-upright
Propagation: Terminal tip cuttings and tissue culture
Time to produce a finished flowering plant: About 14 weeks in the winter under short day conditions, and 6 weeks in the spring
Time to initiate and develop roots: 2 to 3 weeks
Root description: Moderate density, moderate branching, white roots
Inflorescence:

Blooming habit (flowering season): Continuously flowering during spring and summer
Inflorescence type: Sympodial, with monochasial growth
Flowers:

Arrangement: Composed of 5 petals fused at the base
Color: Magenta with white dots scattered throughout the petals, white center, and a slight petal margin
Petals:

Apex: Broadly acute
Base: Fused
Shape: Salverform
Margin: Entire
Strength of waviness: Medium
Degree of lobation: Medium-strong
Calyx arrangement: Actinomorphic, composed of 5 sepals
Reproductive organs:
Stamens:

Quantity: 5
Pistils:

Quantity per flower: 1

Table 2 below shows a comparison between *Petunia* KLEPH20580 and both parental lines.

TABLE 2

Comparison of KLEPH20580 with parental lines

| Characteristic | KLEPH20580 | Female parent 'Wespebimost' | Male Parent 'PH-2017-2906' |
|---|---|---|---|
| Corolla color and pattern | Magenta with white dots scattered throughout the petals, white center, and slight petal margin | Dark-purple with yellow center and slight petal margin | Magenta with white dots scattered throughout the petals |

Table 3 below shows a comparison between *Petunia* KLEPH20580 and commercial variety 'KLEPH15313', U.S. Pat. No. 27,237 and U.S. Pat. No. 10,588,288.

TABLE 3

Comparison of KLEPH20580 with commercial variety

| Characteristic | KLEPH20580 | 'KLEPH15313' |
|---|---|---|
| Flower color | Magenta with white dots scattered throughout the petals, white center, and slight petal margin | Violet-purple with white dots scattered throughout the petals |

Further Embodiments

Spotted Flower Color Pattern—General

The spotted flower color pattern comprises having one or more spots on each petal. The unique spotted flower color pattern comprises spots of a different color than the basic color of the respective flower. The spots may be white, cream, yellow, yellow-green, or combinations thereof in color. The spots may be circular or irregular in shape and may also vary in size. The spotted color pattern may be present on a base flower color of yellow, orange, red, brown, blue, black, pink, violet, or combinations and shades thereof and may be in combination with a different flower pattern comprising a star pattern or a border pattern, including a picotee border pattern. A picotee border is a border around the flower margin/border that is a different color from the rest of the corolla. Thus, one embodiment includes producing a *Petunia* or a *Petunia-Calibrachoa* plant having the spotted color pattern in combination of any of the above star or border patterns, spot colors, and base flower color. A "star pattern" refers to a pattern expressed on the flower where streaks of color longitudinally divide the pigmented sections of the flower. The streaks are sometimes referred to as lines and may be thin or thick and solid or semi-solid. The streaks or lines radiate from the center or approximately the center of the flower towards the outer margin of the flower. The streaks or lines may radiate all the way to the outer margin of the flower or partially towards the outer margin of the flower. The streaks or lines may vary in color and color patterns.

Breeding with *Petunia* KLEPH20580

The goal of ornamental plant breeding is to develop new, unique and superior ornamental plants. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same genetic variety, having the same traits from the exact same parents.

Each year, the plant breeder selects the germplasm to advance to the next generation. This germplasm is grown under unique, different geographical, climatic and soil conditions and further selections are then made during and at the end of the growing season.

Breeding programs combine desirable traits from two or more varieties or various broad-based sources into breeding pools from which varieties are developed by a variety of breeding techniques and selection of desired phenotypes.

Using *Petunia* KLEPH20580 to Develop Other Plants

KLEPH20580 can also provide a source of breeding material that may be used to develop new *Petunia* plants and varieties. Plant breeding techniques known in the art and used in a *Petunia* plant breeding program include, but are not limited to, recurrent selection, crossing, selfing, mass selection, bulk selection, hybridization, backcrossing, pedigree breeding, open-pollination breeding, mutation breeding, restriction fragment length polymorphism enhanced selection, genetic marker enhanced selection, making double haploids, mutagenesis and transformation. Often combinations of these techniques are used. There are many analytical methods available to evaluate a new variety. The oldest and most traditional method of analysis is the observation of phenotypic traits, but genotypic analysis may also be used.

Additional Breeding Methods

Any plants produced using KLEPH20580 as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdø, Marie, "Inter-specific Crosses in *Lupinus*: Cytology and Inheritance of Flower Color," Institute of Genetics and Plant Breeding, Agricultural College of Norway, Vollebekk, Norway (Sep. 28, 1956).

Alone, or in in conjunction with various breeding techniques, other techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which *Petunia* plants can be regenerated, plant calli, plant clumps, and plant cells that are intact in plants or parts of plants, such as pollen, ovules, embryos, protoplasts, meristematic cells, callus, leaves, anthers, cotyledons, hypocotyl, pistils, roots, root tips, seeds, flowers, petiole, shoot, or stems and the like.

Pedigree Breeding

Pedigree breeding starts with the crossing of two genotypes, such as KLEPH20580 and another different *Petunia* having one or more desirable characteristics. If the two original parents do not provide all the desired characteristics, other sources can be included in the breeding population. In the pedigree method, superior plants are selfed or intercrossed and selected in successive filial generations. In the succeeding filial generations, the heterozygous condition gives way to homogeneous varieties as a result of self-pollination and selection.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics and yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a *Petunia* plant may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *Petunia* varieties.

Therefore, another embodiment is a method of making a backcross conversion of KLEPH20580, comprising the steps of crossing KLEPH20580 with a donor plant comprising a desired trait, selecting an $F_1$ progeny plant comprising the desired trait, and backcrossing the selected $F_1$ progeny plant to KLEPH20580. This method may further comprise the step of obtaining a molecular marker profile of KLEPH20580 and using the molecular marker profile to select for a progeny plant with the desired trait and the molecular marker profile of KLEPH20580.

Recurrent Selection and Mass Selection

Recurrent selection is a method used in a plant breeding program to improve a population of plants. KLEPH20580 is suitable for use in a recurrent selection program. The method entails individual plants cross-pollinating with each other to form progeny. The progenies are grown and the superior progenies selected by any number of selection methods, which include individual plant, half-sib progeny, full-sib progeny, and selfed progeny. The selected progenies are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Mutation Breeding

Mutation breeding is another method of introducing new traits into *Petunia* KLEPH20580. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions (also known as somaclonal variation), ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanied by the isolation of chromosomal DNA from every mutated plant line or seed and screening of the population of the seed or plants is performed at the DNA level using advanced molecular techniques. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" *International Journal of Plant Genomics.* 2011 (2011); 13 pages. In addition, mutations created in other *Petunia* plants may be used to produce a backcross conversion of *Petunia* that comprises such mutation.

Mutations that occur spontaneously can also be known as naturally-occurring mutations. These types of mutations are further known as sports, breaks, or chimeras and can be comprised of single cell mutations, branch mutations, or whole plant mutations. Any one of these mutations can change one or more phenotypic characteristics when compared to the original plant. Therefore, another embodiment includes a naturally-occurring genetic mutation of the plant of KLEPH20580, wherein said mutation is comprised from the group consisting of a single cell mutation, branch mutation, or a whole-plant mutation and plants derived from said naturally-occurring mutation or mutations.

Protoplast Fusion

Also known as somatic fusion, this process can be used with KLEPH20580 to create hybrids. The resulting hybrid plants have the chromosomes of each parent and thus the process is useful for incorporating new traits. The protoplast fusion technique is well known in the art; see for example Hamill J. D., Cocking E. C. (1988) Somatic Hybridization of Plants and its Use in Agriculture. In: Pais M. S. S., Mavituna F., Novais J. M. (eds) *Plant Cell Biotechnology.* NATO ASI Series (Series H: Cell Biology), vol 18.

Gene Editing Using CRISPR

Targeted gene editing can be done using CRISPR/Cas9 technology (Saunders & Joung, *Nature Biotechnology,* 32, 347-355, 2014). CRISPR is a type of genome editing system that stands for Clustered Regularly Interspaced Short Palindromic Repeats. This system and CRISPR-associated (Cas) genes enable organisms, such as selected bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. Science 315, 1709-1712 (2007). Many plants have already been modified using the CRISPR system. See for example, U.S. Application Publication No. WO2014068346 (Gyorgy et al., Identification of a *Xanthomonas euvesicatoria* resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science* Vol. 7 Nov. 2016; and "Exploiting the CRISPR/Cas9 System for Targeted Genome Mutagenesis in *Petunia*" *Science Reports* Volume 6: February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on *Petunia* KLEPH20580 to modify traits and resistances or tolerances to pests, herbicides, diseases, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using KLEPH20580. The technique is well known in the art; see for example Malzahn, Aimee et al. "Plant genome editing with TALEN and CRISPR" *Cell & Bioscience* vol. 7 21. 24 Apr. 2017.

Therefore, it is another embodiment to use the TALENs system on *Petunia* variety KLEPH20580 to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant*. 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on *Petunia* variety KLEPH20580 to modify traits and resistances or tolerances to pests, herbicides, and viruses.

Foreign Protein Genes: Transformation

Various promoters, targeting sequences, enhancing sequences, and other DNA sequences can be inserted into the genome for the purpose of altering the expression of genes.

Many techniques for altering gene expression are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., PNAS USA, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., Antisense Res. Dev., 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, *Current opinion in plant biology*, Vol: 42, Page: 23-29, 2018 and Eric T. Johnson, Jesse B. Owens & Stefan Moisyadi (2016) Vast potential for using the piggy-Bac transposon to engineer transgenic plants at specific genomic locations, Bioengineered, 7:1, 3-6) and other methods or combinations of the above methods known to those of skill in the art.

Additional Methods of Transformation

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject *Petunia* KLEPH20580 plants are intended to be within the scope of the embodiments of the application.

Introduction of a New Trait or Locus into *Petunia* KLEPH20580

*Petunia* KLEPH20580 represents a new base of genetics into which a new locus, gene, or trait may be introgressed. Direct transformation and backcrossing represent two important methods that can be used to accomplish such an introgression, but additional gene editing techniques also exist. The term backcross conversion and single locus conversion are used interchangeably.

When the term *Petunia* KLEPH20580 plant is used in the context of an embodiment of the present application, this also includes any single gene conversions of *Petunia* KLEPH20580. The term single gene converted plant as used herein refers to those *Petunia* plants which are developed by a plant breeding technique called backcrossing wherein essentially all of the desired morphological and physiological characteristics of a variety are recovered in addition to the single gene transferred into the variety.

Backcross Conversions of *Petunia* KLEPH20580

The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental *Petunia* plant that contributes the gene for the desired characteristic is termed the nonrecurrent or donor parent. This terminology refers to the fact that the nonrecurrent parent is used one time in the backcross protocol and therefore does not recur. The parental *Petunia* plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Petunia* plant is obtained wherein essentially all of the desired morphological and physiological characteristics of the recurrent parent are recovered in the converted plant, in addition to the single transferred gene from the nonrecurrent parent.

A backcross conversion of *Petunia* KLEPH20580 occurs when DNA sequences are introduced through backcrossing (Allard, "Principles of Plant Breeding" (1999) with *Petunia* KLEPH20580 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding"

(1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety. In some embodiments, the number of loci that may be backcrossed into Petunia KLEPH20580 is at least 1, 2, 3, 4, or 5, and/or no more than 6, 5, 4, 3, or 2.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny Petunia seed by adding a step at the end of the process that comprises crossing Petunia KLEPH20580 with the introgressed trait or locus with a different plant and harvesting the resultant first generation progeny seed.

Molecular Techniques Using Petunia KLEPH20580

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a breeding program. The markers can also be used to select for the genome of the recurrent parent and against the genome of the donor parent, in for example, a backcross breeding program. Using this procedure can minimize the amount of genome from the donor parent that remains in the selected plants. It can also be used to reduce the number of crosses back to the recurrent parent needed in a backcrossing program.

The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing Petunia KLEPH20580. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in Brassica napus" Journal of Experimental Biology. 66 (1): 245-256 (2014).

QTL markers can also be used during the breeding process for the selection of qualitative traits. For example, markers closely linked to alleles or markers containing sequences within the actual alleles of interest can be used to select plants that contain the alleles of interest during a breeding program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Tissue Culture

Further reproduction of the variety can occur by tissue culture and regeneration. Tissue culture of various tissues of ornamental plants and Petunia KLEPH20580 and regeneration of plants therefrom is well-known and widely published. See, for example, Valla Rego, Luciana et al., Crop Breeding and Applied Technology. 1(3): 283-300 (2001); Komatsuda, T., et al., Crop Sci., 31:333-337 (1991); Stephens, P. A., et al., Theor. Appl. Genet., 82:633-635 (1991); Komatsuda, T., et al., Plant Cell, Tissue and Organ Culture, 28:103-113 (1992); Dhir, S., et al., Plant Cell Reports, 11:285-289 (1992); Pandey, P., et al., Japan J. Breed., 42:1-5 (1992); and Shetty, K., et al., Plant Science, 81:245-251 (1992). Thus, another embodiment is to provide cells which upon growth and differentiation produce Petunia plants having the physiological and morphological characteristics of Petunia KLEPH20580 described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, leaves, anthers, cotyledons, hypocotyl, pistils, roots, root tips, flowers, seeds, petiole, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

A deposit of the Klemm+Sohn GmbH & Co. KG proprietary *Petunia* KLEPH20580 plant tissue disclosed above and recited in the appended claims has been made with and accepted by the Provasoli-Guillard National Center for Marine Algae and Microbiota, Bigelow Laboratory for Ocean Sciences (NCMA), 60 Bigelow Drive, East Boothbay, Me. 04544. The date of deposit was Apr. 27, 2021. The NCMA No. is 202104022. The deposit of plant tissue was taken from the same deposit maintained by Klemm+Sohn GmbH & Co. KG since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A plant of *Petunia* variety KLEPH20580, having a spotted flower color pattern, wherein a representative sample of plant tissue of said variety was deposited under NCMA No. 202104022.

2. A plant, or a plant part thereof, produced by growing a plant of *Petunia* variety KLEPH20580, wherein a representative sample of plant tissue of said variety was deposited under NCMA No. 202104022, and wherein the plant or plant part comprises at least one cell of *Petunia* variety KLEPH20580.

3. A *Petunia* plant, or part thereof, having all of the physiological and morphological characteristics of the *Petunia* plant of claim 1.

4. A tissue or cell culture of regenerable cells produced from the plant or plant part of claim 2.

5. A *Petunia* plant regenerated from the tissue or cell culture of claim 4, wherein said plant has all of the morphological and physiological characteristics of *Petunia* variety KLEPH20580.

6. A method of vegetatively propagating the plant of claim 1, comprising the steps of:
    collecting tissue or cells capable of being propagated from said plant;
    cultivating said tissue or cells to obtain proliferated shoots or plantlets; and
    rooting said proliferated shoots or plantlets to obtain rooted shoots or rooted plantlets.

7. A *Petunia* plant produced by growing the rooted shoots or rooted plantlets of claim 6.

8. A method for producing a seed or embryo, wherein the method comprises crossing *Petunia* variety KLEPH20580, wherein a representative sample of plant tissue of said variety was deposited under NCMA No. 202104022, with a different plant and harvesting the resultant seed or embryo.

9. A method of determining the genotype of the *Petunia* plant of claim 1, wherein said method comprises obtaining a sample of nucleic acids from said plant and detecting in said nucleic acids a plurality of polymorphisms.

10. A method of introducing a mutation into the genome of a KLEPH20580 plant, said method comprising mutagenesis of the plant, or plant part thereof, of claim 1, wherein said method of mutagenesis is selected from the group consisting of temperature, long term seed storage, somaclonal variation, radiation, chemical agents, targeting induced local lesions in genomes, site-directed mutagenesis, and genome editing, and wherein the resulting plant comprises at least one genome mutation.

11. A method of genetically modifying the plant of claim 1, wherein said genetic modification is selected from *Agro*- bacterium-mediated gene transfer, protoplast transformation, or biolistic transformation.

12. A plant produced by the method of claim 11, wherein said plant has the spotted flower color pattern.

13. A method for producing a seed or embryo, wherein the method comprises selfing *Petunia* variety KLEPH20580, wherein a representative sample of plant tissue of said variety was deposited under NCMA No. 202104022, and harvesting the resultant seed or embryo.

14. A plant produced by growing the seed or embryo produced by the method of claim 13, wherein said plant has the spotted color flower pattern.

15. A method for developing a *Petunia* plant having a spotted flower color pattern, wherein said method comprises applying plant breeding techniques to the plant of *Petunia* variety KLEPH20580, having a spotted flower color pattern, wherein a representative sample of plant tissue of said variety was deposited under NCMA No. 202104022, to produce a plant having a spotted flower color pattern.

16. The method of claim 15, wherein said plant breeding technique is recurrent selection.

17. The method of claim 15, wherein said plant breeding technique is mass selection.

18. The method of claim 15, wherein said plant breeding technique is hybridization.

19. The method of claim 15, wherein said plant breeding technique is open-pollination.

20. The method of claim 15, wherein said plant breeding technique is backcrossing.

21. The method of claim 15, wherein said plant breeding technique is pedigree breeding.

22. The method of claim 15, wherein said plant breeding technique is mutation breeding, and wherein said mutation selected is spontaneous or artificially induced.

23. The method of claim 15, wherein said plant breeding technique is genetic marker enhanced selection.

24. A method of editing the genome of *Petunia* plant KLEPH20580, said method comprising editing the genome of the plant of claim 1, or a part thereof, wherein said method is selected from the group consisting of zinc finger nucleases, transcription activator-like effector nucleases (TALENs), engineered homing endonucleases/meganucleases, and the clustered regularly interspaced short palindromic repeat (CRISPR)-associated protein9 (Cas9) system.

25. A *Petunia* plant produced by the method of claim 24.

26. A *Petunia* seed produced by growing the plant of claim 1.

27. A method of producing a *Petunia* plant, or part thereof, produced by growing the seed of claim 26.

* * * * *